United States Patent
Kim et al.

(10) Patent No.: US 11,896,685 B2
(45) Date of Patent: Feb. 13, 2024

(54) CORE-SHELL NETWORK STRUCTURE COMPRISING BIOPOLYMER AND COMPOSITION COMPRISING SAME

(71) Applicant: AMOREPACIFIC CORPORATION, Seoul (KR)

(72) Inventors: Eunmi Kim, Yongin-si (KR); Young Gyu Kang, Yongin-si (KR); Jaeyoung Ko, Yongin-si (KR); Miju Kim, Yongin-si (KR); Minkee Kim, Yongin-si (KR); Yong Jin Kim, Yongin-si (KR); Heungsoo Baek, Yongin-si (KR); Jaewon You, Yongin-si (KR); Yonghee Lee, Yongin-si (KR); Eun Soo Lee, Yongin-si (KR); Yuri Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 503 days.

(21) Appl. No.: 17/290,131

(22) PCT Filed: Oct. 31, 2019

(86) PCT No.: PCT/KR2019/014590
§ 371 (c)(1),
(2) Date: Apr. 29, 2021

(87) PCT Pub. No.: WO2020/091456
PCT Pub. Date: May 7, 2020

(65) Prior Publication Data
US 2021/0393489 A1    Dec. 23, 2021

(30) Foreign Application Priority Data

Oct. 31, 2018  (KR) .................. 10-2018-0132495
Oct. 30, 2019  (KR) .................. 10-2019-0136397

(51) Int. Cl.
*A61K 8/02*     (2006.01)
*A61K 8/64*     (2006.01)
(Continued)

(52) U.S. Cl.
CPC ............ *A61K 8/0233* (2013.01); *A61K 8/645* (2013.01); *A61K 8/73* (2013.01); *A61Q 19/00* (2013.01);
(Continued)

(58) Field of Classification Search
None
See application file for complete search history.

(56) References Cited

U.S. PATENT DOCUMENTS

| 8,658,200 B2 | 2/2014 | Mody et al. |
| 2006/0147542 A1 | 7/2006 | Ono et al. |

(Continued)

FOREIGN PATENT DOCUMENTS

| CN | 103957893 A | 7/2014 |
| CN | 106692978 A | 5/2017 |

(Continued)

OTHER PUBLICATIONS

Dhanya, AT, et al., Development of Zein-Pectin Nanoparticle as Drug carrier, Int. J. Drug Del., 4 (2012) pp. 147-152. (Year: 2012).*

(Continued)

*Primary Examiner* — Dominic Lazaro
(74) *Attorney, Agent, or Firm* — MERCHANT & GOULD P.C.

(57) ABSTRACT

The present invention relates to a core-shell network structure formed using a biocompatible biopolymer and to a composition comprising same. Said structure can be used as an alternative to synthetic chemical materials, such as polyethylene glycol (PEG), to effectively disperse an insoluble effective substance within a composition, thus addressing (Continued)

Schematic of core-shell network

| Core | | Shell network | |
|---|---|---|---|
| Insoluble effective substance | Prolamin | Pullulan | Pectin | safety issues, and formulations can be preserved stably for a long time through said network structure. Furthermore, said structure and the composition comprising same may provide useful benefits for the skin in terms of skin barrier enhancement, skin moisturization, skin regeneration, or the like.

20 Claims, 17 Drawing Sheets

(51) Int. Cl.
    *A61K 8/73*         (2006.01)
    *A61Q 19/00*       (2006.01)

(52) U.S. Cl.
    CPC .. *A61K 2800/594* (2013.01); *A61K 2800/622* (2013.01); *A61K 2800/652* (2013.01)

(56) References Cited

U.S. PATENT DOCUMENTS

| | | | |
|---|---|---|---|
| 2007/0110799 | A1 | 5/2007 | Leferve et al. |
| 2015/0342896 | A1 | 12/2015 | Koyakutty et al. |
| 2017/0119803 | A1 | 5/2017 | Koyakutty et al. |
| 2017/0333365 | A1 | 11/2017 | Koyakutty et al. |
| 2019/0336931 | A1 | 11/2019 | Lagaron Cabello et al. |
| 2021/0161830 | A1 | 6/2021 | Kim et al. |

FOREIGN PATENT DOCUMENTS

| | | |
|---|---|---|
| CN | 112891244 A | 6/2021 |
| EP | 2292102 A1 | 3/2011 |
| EP | 2591772 A1 | 5/2013 |
| JP | H09-252744 A | 9/1997 |
| JP | 2015-518370 A | 7/2015 |
| KR | 10-2003-0070799 A | 9/2003 |
| KR | 10-2005-0042873 A | 5/2005 |
| KR | 10-0648535 B1 | 11/2006 |
| KR | 10-2007-0091680 A | 9/2007 |
| KR | 10-2014-0041453 A | 4/2014 |
| KR | 10-2014-0091054 A | 7/2014 |
| KR | 10-2017-0080671 A | 7/2017 |
| WO | 2005/060944 A1 | 7/2005 |
| WO | 2012/116282 A2 | 8/2012 |
| WO | 2013/068478 A1 | 5/2013 |
| WO | 2013/141964 A1 | 9/2013 |
| WO | 2014197640 A1 | 12/2014 |
| WO | 2016/071466 A1 | 5/2016 |

OTHER PUBLICATIONS

Webpage—Liposomes, http://www.nanovec.com/en/liposomes, retrieved 2022.

Y. Luo et al., "Zein-Based Micro- and Nano-Particles for Drug and Nutrient Delivery: A Review", Journal of Applied Polymer Science: 1-12 (2014).

X. Huang et al., "Encapsulation of Resveratrol in Zein/pectin Core-shell Nanoparticles: Stability, Bioaccessibility, and Antioxidant Capacity after Simulated Gastrointestinal Digestion", Food Hydrocolloids, vol. 93: 261-269 (2019).

Y. Zhang et al, "Fabrication, characterization and antimicrobial activities of thymolloaded zein nanoparticles stabilized by sodium caseinate-chitosan hydrochloride double layers", Food Chemistry, vol. 142: 269-275 (2014).

Xulin et al., "Study on the preparation and biological activity of curcumin loaded zein/polysaccharide nanoparticles", Journal of Guangdong Pharmaceutical University, 2016, vol. 32, No. 5, pp. 545-549.

Liu et al., "Pectin/Zein Beads for Potential Colon-Specific Drug Delivery: Synthesis and in Vitro Evaluation", Drug Delivery, 2006, vol. 13, No. 6, pp. 417-423.

Office Action for Chinese Application No. 201980072732.2 (dated Jan. 13, 2022).

Dhanya AT et al.: "Development of Zein-Pectin Nanoparticle as Drug carrier", International Journal of Drug Delivery, vol. 4: 147-152 (2012).

Hu K et al.: "Core-shell biopolymer nanoparticle delivery systems: Synthesis and characterization of curcumin fortified zein-pectin nanoparticles", Food Chemistry, vol. 182: 275-281 (2015).

Mukhidinov Z.K. et al.: "Pectin-Zein Microspheres as Drug Delivery Systems", Pharmaceutical Chemistry Journal, vol. 44 (10): 564-567 (2011).

Liu S.C. et al.: "Electrospun Food-Grade Ultrafine Fibers from Pectin and Pullulan Blends", Food and Nutrition Sciences, 7: 636-646 (2016).

Trevino-Garza M.Z. et al.: "Edible Active Coatings Based on Pectin, Pullulan, and Chitosan Increase Quality and Shelf Life of Strawberries (*Fragaria ananassa*)", Journal of Food Science, vol. 80 (8): M1823-M1830 (2015).

International Search Report PCT/KR2019/014590, dated Feb. 7, 2020.

* cited by examiner

Schematic of core-shell network

| Core | | Shell network | |
|---|---|---|---|
| Insoluble effective substance | Prolamin | Pullulan | Pectin |

On day of preparation (Left) Example 2 / RT (Center) Example 2 / Cycle (Right) Example 2 / 60°C On day of preparation (Left) Example 1 / RT
(Center) Example 1 / Cycle
(Right) Example 1 / 60°C 1 month later (Left) Example 2 / RT
(Center) Example 2 / Cycle
(Right) Example 2 / 60°C 1 month later (Left) Example 1 / RT
(Center) Example 1 / Cycle
(Right) Example 1 / 60°C

CORE-SHELL NETWORK STRUCTURE COMPRISING BIOPOLYMER AND COMPOSITION COMPRISING SAME

CROSS-REFERENCE TO RELATED APPLICATIONS

This application is a National Stage Application of PCT/KR2019/014590, filed Oct. 31, 2019, which claims benefit of priority to Korean Patent Application No. 10-2018-0132495 filed on Oct. 31, 2018 and Korean Patent Application No. 10-2019-0136397 filed on Oct. 30, 2019, which applications are incorporated herein by reference. To the extent appropriate, a claim of priority is made to each of the above disclosed applications.

TECHNICAL FIELD

The present disclosure relates to a structure using a biopolymer and a composition comprising the same.

BACKGROUND ART

When an insoluble effective substance such as ginseng saponin, bean saponin, epigallocatechin gallate (EGCG), etc. is comprised in a cosmetic formulation, the effect of the effective substance may not be exhibited as the substance is separated or deposited due to poor formulation stability or the appearance or usability may be unsatisfactory. Therefore, in the cosmetic industry or pharmaceutical industry, a nanoemulsion formulation is prepared by encapsulating the insoluble effective substance using a solubilizer in order to introduce it into a cosmetic or pharmaceutical formulation, or the effective substance is dispersed inside microcapsules. In general, polyethylene glycol (PEG) is the most widely used as a solubilizer for solubilizing the insoluble effective substance and maximizing its effect.

Recently, however, due to safety issues such as the toxicity and allergenicity of polyethylene glycol suggested by several studies, the use of polyethylene glycol is avoided in the cosmetic industry or pharmaceutical industry. In the pharmaceutical industry, researches are already ongoing to replace PEGylation with PASylation using proline-alanine-serine repeats. Also, in the cosmetic industry, with the chemophobia issue, needs on a substance capable of replacing polyethylene glycol is increasing. Therefore, development of a natural, biocompatible solubilizing system which can stably solubilize insoluble effective substances is necessary.

REFERENCES OF RELATED ART

Patent Document (Patent document 1) Korean Patent Registration Publication No. 10-0648535

DISCLOSURE

Technical Problem

In an aspect, the present disclosure is directed to providing a structure using a biopolymer, which is biocompatible and can effectively solubilize an insoluble effective substance, and a composition comprising the same.

In an aspect, the present disclosure is directed to providing a composition comprising the structure using a biopolymer, which provides useful benefits for skin.

Technical Solution

In an aspect, the present disclosure provides a core-shell network structure comprising a core-shell particle formed of: a core comprising prolamin; and a shell comprising pullulan and pectin, wherein an interconnected network is formed between the core-shell particles as the pullulan surrounds the core and the pectin is located at an outermost layer of the shell, or a composition comprising the same.

In an aspect, the present disclosure provides a composition for solubilizing an insoluble effective substance, which comprises the core-shell network structure.

In an aspect, the present disclosure provides a composition for one or more of skin barrier enhancement, skin moisturization and skin regeneration, which comprises the core-shell network structure as an active ingredient.

In an aspect, the present disclosure provides a composition comprising a core-shell network structure comprising: a core comprising an insoluble effective substance and prolamin; and a shell comprising pullulan and pectin, wherein an interconnected network is formed between the core-shell particles as the pullulan surrounds the core and the pectin is located at an outermost layer of the shell.

In another aspect, the present disclosure provides a method for preparing the structure, which comprises: a step of forming a core by dispersing prolamin in an alcohol solvent; a step of forming a shell surrounding the core by adding pullulan onto the alcohol solution in a drop-by-drop manner; a step of coating pectin on an outermost layer of the shell and forming a network between the shell by adding pectin to the pullulan-added alcohol solution; and a step of obtaining a solution with a core-shell network structure dissolved in an aqueous phase formed by evaporating the alcohol from the pectin-added solution.

Advantageous Effects

In an aspect, since the present disclosure allows solubilization of an insoluble effective substance with a core-shell network structure formed using a biocompatible biopolymer, the safety issue of the existing synthetic chemical substance used as a solubilizer, such as polyethylene glycol (PEG), can be resolved. The structure in which a network is formed between the shells of core-shell nanoparticles serves as a support, thereby allowing uniform distribution of the core-shell nanoparticles in a composition and stable maintenance of a formulation for a long time. In addition, the present disclosure may provide the effects of skin barrier enhancement, skin moisturization and skin regeneration using the core-shell network structure.

BEST MODE

Figure 1:
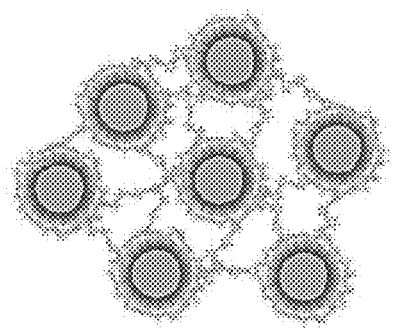
FIG. 1 schematically shows a core-shell network structure comprised in a composition according to an example of the present disclosure.

Hereinafter, exemplary embodiments of the present disclosure will be described in more detail referring to the attached drawings. However, the technology disclosed in the present disclosure is not limited to the exemplary embodiments described herein but may be embodied in other forms. The exemplary embodiments are provided so that the present disclosure is thorough and complete, and will fully convey the technical idea of the present disclosure to those skilled in the art. In the drawings, the width, thickness, etc. of each element are somewhat exaggerated to emphasize the element. In addition, although only a part is shown for some elements, the remaining part may be easily understood by those skilled in the art. In addition, those having ordinary knowledge in the art may embody the technical idea of the present disclosure in various other forms without departing from the scope of the technical idea of the present disclosure.

FIG. 1 schematically describes a core-shell network structure according to an exemplary embodiment of the present disclosure. Referring to FIG. 1, the core-shell network structure according to an exemplary embodiment of the present disclosure is formed using a biopolymer, wherein the core may comprise prolamin and the shell may comprise pullulan and pectin. An interconnected network may be formed between the core-shell particles as the pullulan surrounds the core and the pectin is located at an outermost layer of the shell.

In the present disclosure, the core-shell network structure with the interconnected network formed between the core-shell particles is named "Ecoweb".

In addition, in an exemplary embodiment, the present disclosure may provide a composition for solubilizing an insoluble effective substance, which comprises the core-shell network structure. In an exemplary embodiment, the insoluble effective substance may refer to a substance which is hydrophobic and alcohol-soluble. In another exemplary embodiment, the present disclosure may provide a use of the core-shell network structure for preparing a composition for solubilizing an insoluble effective substance. In another exemplary embodiment, the present disclosure may provide a method for solubilizing an insoluble effective substance, which comprises adding an effective amount of the core-shell network structure to a composition comprising the insoluble effective substance. In another exemplary embodiment, the present disclosure may provide the core-shell network structure as an active ingredient for use in a composition for solubilizing an insoluble effective substance.

In the present disclosure, the term "biopolymer" is also called "biological polymer" and is contrasted with "synthetic polymer". The term biopolymer refers to a polymer substance constituting an organism or produced by an organism, and is used in the broadest concept, comprising nucleic acids, polysaccharides, proteins, etc.

In the present disclosure, the prolamin is a simple plant protein having a high glutamine and proline content. It has self-assembling hydrophobicity due to hydrophobic amino acids such as leucine, isoleucine, etc. distributed on the surface. Accordingly, the prolamin can effectively capture an insoluble effective substance by forming a brick-like structure around the insoluble effective substance. In an exemplary embodiment, the prolamin may be one or more selected from a group consisting of zein, hordein, secalin, kafirin, gliadin, oryzin and avenin, but any prolamin may be used without being limited thereto. Specifically, zein may be isolated or extracted from corn, hordein from barley, secalin from rye, kafirin from sorghum, gliadin from wheat, oryzin from rice, and avenin from oats.

In an exemplary embodiment, the structure may comprise the prolamin in an amount of 0.025-7.5 wt % based on the total weight of the core-shell network structure. Also, in an exemplary embodiment, the prolamin may be comprised in an amount of 0.01-3 wt % based on the total weight of the composition. The prolamin serves as a core of a Pickering emulsion through hydrophobic interaction with the insoluble effective substance. When the amount of the prolamin exceeds the range described above, the insoluble effective substance and the prolamin may form a large aggregated precipitate instead of a plurality of core-shell particles. As a result, the network structure is not formed and the formulation is separated into insoluble and soluble parts. Specifically, the prolamin may be comprised in an amount of 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more or 3 wt % or more, based on the total weight of the composition. In an exemplary embodiment, the prolamin may be comprised in an amount of 3 wt % or less, 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In the present disclosure, the pullulan is a substance obtained by isolating and purifying a polysaccharide from black yeast (fungus *Aureobasidium pullulans*). It may consist of maltotriose, which is a trisaccharide consisting of three glucose molecules linked with α-1,4 glycosidic bonds. It is hydrophilic and dissolves well in water, but is insoluble in alcohols. With coating ability and adhesivity, it can form a core-shell structure by coating the core comprising prolamin.

In an exemplary embodiment, the structure may comprise the pullulan in an amount of 0.025-12.5 wt % based on the total weight of the core-shell network structure. Also, in an exemplary embodiment, the pullulan may be comprised in an amount of 0.01-5 wt % based on the total weight of the composition. When the pullulan is comprised in an amount within the above-described range, primary solubilization stability may be provided because a coat may be formed effectively on the core. When the pullulan is comprised in an amount less than 0.01 wt %, the core-shell structure may not be formed effectively in the composition and the insoluble effective substance may be precipitated. Specifically, the pullulan may be comprised in an amount of 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more or 5 wt % or more, based on the total weight of the composition. In an exemplary embodiment, the pullulan may be comprised in an amount of 5 wt % or less, 4 wt % or less, 3 wt % or less, 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In the present disclosure, the pectin is a hydrated gel surrounding a cellulose-hemicellulose network in a plant. It is a polysaccharide whose main component is galacturonic acid, an oxidized form of galactose. When the core-shell structure consists only of prolamin and pullulan and a very small amount of the insoluble effective substance is comprised therein, increasing the content of the effective substance may result in a solubilized state in which the core shell is precipitated due to its weight. In contrast, according to the present disclosure, an interconnected network of the core-shell particle is formed as the pectin is comprised in the shell and, therefore, the core-shell particle may be supported stably and the degree of precipitation may be minimized. Accordingly, the insoluble effective substance at a high content may be supported stably for a long period of time and the substance may be uniformly dispersed and solubilized in the formulation of the composition.

In an exemplary embodiment, the structure may comprise the pectin in an amount of 0.05-10 wt % based on the total weight of the core-shell network structure. Also, in an exemplary embodiment, the pectin may be comprised in an amount of 0.01-2 wt % based on the total weight of the composition. When the pectin is comprised in an amount within the above-described range, secondary solubilization stability may be provided as a physically stable structure is formed between the core-shell particles. When the pectin is comprised in an amount less than 0.01 wt %, the insoluble effective substance may be precipitated as the network supporting the core-shell particle is not formed stably.

Specifically, the pectin may be comprised in an amount of 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more or 2 wt %, based on the total weight of the composition. The pectin may be comprised in an amount of 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In an exemplary embodiment, the core-shell particle may have an average particle size of greater than 100 nm and 600 nm or smaller. The average particle size means the average of the largest diameter of particles, and the average of the particle size means the average of at least 90% of the core-shell particles distributed in the structure or composition. Specifically, the average of the particle size may mean the average of the largest diameter of at least 90%, at least 91%, at least 92%, at least 93%, at least 94%, at least 95%, at least 96%, at least 97%, at least 98% or at least 99% of the particles distributed in the structure or composition. In the present disclosure, since the hydrophobic core is coated with the hydrophilic polysaccharides comprising pullulan and pectin and the core-shell particles are densely interconnected with each other, the structure wherein particles with an average particle size of greater than 100 nm and 600 nm or smaller are distributed uniformly may be maintained stably in a composition comprising the core-shell network structure for a long time without precipitation. Specifically, the average particle size of the core-shell particle may be 101 nm or larger, 150 nm or larger, 200 nm or larger, 250 nm or larger, 300 nm or larger, 350 nm or larger, 400 nm or larger, 450 nm or larger, 500 nm or larger or 550 nm or larger. Specifically, the average particle size of the core-shell particle may be 600 nm or smaller, 550 nm or smaller, 500 nm or smaller, 450 nm or smaller, 400 nm or smaller, 350 nm or smaller, 300 nm or smaller, 250 nm or smaller, 200 nm or smaller or 150 nm or smaller.

Also, in an exemplary embodiment, the composition comprising the biocompatible biopolymer may enhance the skin barrier by promoting the proliferation of skin cells. Specifically, in an exemplary embodiment, the present disclosure may provide a composition for skin barrier enhancement, which comprises the core-shell network structure as an active ingredient. In another exemplary embodiment, the present disclosure may provide a use of the core-shell network structure for use in preparing a composition for skin barrier enhancement. In another exemplary embodiment, the present disclosure may provide a method for skin barrier enhancement, which comprises administering an effective amount of the core-shell network structure to a subject in need thereof. In another exemplary embodiment, the method may comprise administering the core-shell network structure to a subject with declined skin barrier recovery function. In another exemplary embodiment, the present disclosure may provide the core-shell network structure as an active ingredient for use in a composition for skin barrier enhancement. In addition, the present disclosure may provide a non-therapeutic use of the core-shell network structure as an active ingredient for skin barrier enhancement.

In an exemplary embodiment, the present disclosure may provide a composition for skin moisturization, which comprises the core-shell network structure as an active ingredient. In another exemplary embodiment, the present disclosure may provide a use of the core-shell network structure for use in preparing a composition for skin moisturization. In another exemplary embodiment, the present disclosure may provide a method for skin moisturization, which comprises administering an effective amount of the core-shell network structure to a subject in need thereof. In another exemplary embodiment, the present disclosure may provide the core-shell network structure as an active ingredient for use in a composition for skin moisturization. In addition, the present disclosure may provide a non-therapeutic use of the core-shell network structure as an active ingredient for skin moisturization.

In an exemplary embodiment, the present disclosure may provide a composition for skin regeneration, which comprises the core-shell network structure as an active ingredient. In another exemplary embodiment, the present disclosure may provide a use of the core-shell network structure for use in preparing a composition for skin regeneration. In another exemplary embodiment, the present disclosure may provide a method for skin regeneration, which comprises administering an effective amount of the core-shell network structure to a subject in need thereof. In another exemplary embodiment, the method may comprise administering the core-shell network structure to a subject with declined skin regeneration function or having skin wound. In another exemplary embodiment, the present disclosure may provide the core-shell network structure as an active ingredient for use in a composition for skin regeneration. In addition, the present disclosure may provide a non-therapeutic use of the core-shell network structure as an active ingredient for skin regeneration.

In an exemplary embodiment, the composition for skin barrier enhancement, skin moisturization or skin regeneration may comprise the core-shell network structure in an amount of 0.005 wt % or more and less than 1 wt % based on the total weight of the composition. Specifically, the composition may comprise the core-shell network structure in an amount of 0.005 wt % or more, 0.006 wt % or more, 0.007 wt % or more, 0.008 wt % or more, 0.009 wt % or more, 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more or 0.9 wt % or more, based on the total weight of the composition. In addition, the composition may comprise the core-shell network structure in an amount of less than 1.0 wt %, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less, 0.01 wt % or less, 0.009 wt % or less, 0.008 wt % or less, 0.007 wt % or less or 0.006 wt % or less, based on the total weight of the composition.

In an exemplary embodiment, an administration dosage of the core-shell network structure may be 1 mg/kg/day to 1 g/kg/day. In an exemplary embodiment, the administration dosage of the core-shell network structure may vary depending on the age, sex and body weight of a subject, the particular disease or pathological condition of the subject, the severity of the disease or pathological condition, administration route, etc., and the determination of the administration dosage based on these factors is within the level of those skilled in the art. For example, the administration dosage may be 1 mg/kg/day or more, 2 mg/kg/day or more, 3 mg/kg/day or more, 4 mg/kg/day or more, 5 mg/kg/day or more, 10 mg/kg/day or more, 20 mg/kg/day or more, 30 mg/kg/day or more, 40 mg/kg/day or more, 50 mg/kg/day or more, 60 mg/kg/day or more, 70 mg/kg/day or more, 80 mg/kg/day or more, 90 mg/kg/day or more, 100 mg/kg/day or more, 110 mg/kg/day or more, 120 mg/kg/day or more, 130 mg/kg/day or more, 140 mg/kg/day or more, 150 mg/kg/day or more, 160 mg/kg/day or more, 170 mg/kg/day or more, 180 mg/kg/day or more, 190 mg/kg/day or more, 200 mg/kg/day or more, 250 mg/kg/day or more, 300 mg/kg/day or more, 350 mg/kg/day or more, 400 mg/kg/day or more, 450 mg/kg/day or more or 500 mg/kg/day or more. In addition, the administration dosage may be, for example, 1 g/kg/day or less, 500 mg/kg/day or less, 450 mg/kg/day or less, 400 mg/kg/day or less, 350 mg/kg/day or less, 300 mg/kg/day or less, 250 mg/kg/day or less, 200 mg/kg/day or less, 190 mg/kg/day or less, 180 mg/kg/day or less, 170 mg/kg/day or less, 160 mg/kg/day or less, 150 mg/kg/day or less, 140 mg/kg/day or less, 130 mg/kg/day or less, 120 mg/kg/day or less, 110 mg/kg/day or less or 100 mg/kg/day or less. However, the administration dosage does not limit the scope of the present disclosure in any way.

In an exemplary embodiment, the present disclosure may provide a composition comprising the core-shell network structure and further comprising an insoluble effective substance (K) in the core of the structure, wherein the insoluble effective substance is captured by the prolamin of the core.

In the present disclosure, the insoluble effective substance refers to a hydrophobic substance which provides beneficial effects for skin or body and is difficult to be dispersed in water. In an exemplary embodiment, it may be a substance which is hydrophobic and alcohol-soluble. For example, the insoluble effective substance may comprise: a triterpenoid comprising one or more selected from a group consisting of oleanolic acid, ursolic acid and arjunolic acid; a polyphenol or a polyphenol derivative comprising one or more selected from a group consisting of amentoflavone, ellagic acid, apigenin, bergenin, diosmetin, univestin, resveratrol, isoflavone and catechin; an oily fatty acid comprising one or more selected from a group consisting of salicylic acid, α-lipoic acid, caffeine, tocopherol, docosahexaenoic acid (DHA), eicosapentaenoic acid (EPA) and conjugated linolenic acid (CLA); a sphingolipid comprising one or more selected from a group consisting of sphingomyelin, ganglioside, cerebroside, ceramide, glycosyl ceramide, lactosyl ceramide, galactosyl ceramide and xylosyl ceramide; a saponin comprising compound K (20-O-β-D-glucopyranosyl-20(S)-protopanaxadiol); carotene or a carotene derivative; and a natural extract comprising one or more selected from a group consisting of ginkgo leaf extract and red ginseng extract. However, the insoluble effective substance is not limited as long as it is a hydrophobic and alcohol-soluble substance.

In an exemplary embodiment, the insoluble effective substance may be comprised in an amount of 0.01-5 wt % based on the total weight of the composition. When the insoluble effective substance is comprised in an amount less than 0.01 wt %, the desired effect of the insoluble effective substance may not be exhibited sufficiently. And, when the insoluble effective substance is comprised in an amount exceeding 5 wt %, the formation of the core-shell particle may be hindered and the core-shell network structure of the present disclosure may be disrupted as the insoluble effective substance is precipitated as a result of hydrophobic interaction with prolamin. Specifically, the insoluble effective substance may be comprised in an amount of 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more or 5 wt % or more, based on the total weight of the composition. In an exemplary embodiment, the insoluble effective substance may be comprised in an amount of 5 wt % or less, 4 wt % or less, 3 wt % or less, 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In an exemplary embodiment, the composition may be for one or more of skin barrier enhancement, skin moisturization and skin regeneration.

In an exemplary embodiment, the present disclosure may provide a method for preparing the structure or a composition comprising the structure. In an exemplary embodiment, the method may comprise: a step of forming a core by dispersing prolamin in an alcohol solvent; a step of forming a shell surrounding the core by adding pullulan onto the alcohol solution in a drop-by-drop manner; a step of coating pectin on an outermost layer of the shell and forming a network between the shells by adding pectin to the pullulan-added alcohol solution; and a step of obtaining a solution with a core-shell network structure dissolved in an aqueous phase by evaporating the alcohol from the pectin-added solution.

In an exemplary embodiment, the present disclosure may provide a method for preparing a composition comprising the core-shell network structure with the insoluble effective substance captured. In an exemplary embodiment, the method may comprise: a step of forming a core by dispersing prolamin and an insoluble effective substance in an alcohol solvent; a step of forming a shell surrounding the core by adding pullulan onto the alcohol solution in a drop-by-drop manner; a step of coating pectin on an outermost layer of the shell and forming a network between the shells by adding pectin to the pullulan-added alcohol solution; and a step of obtaining a solution with a core-shell network structure dissolved in an aqueous phase by evaporating the alcohol from the pectin-added solution.

In an exemplary embodiment, the step of dispersing prolamin and an insoluble effective substance in an alcohol solvent may comprise adding prolamin to an alcohol solvent and then adding and dispersing an insoluble effective substance.

The prolamin is a simple protein which is soluble in 60-90% alcohol. It is soluble in dilute alcohol, but not in water or an anhydrous alcohol solution. Accordingly, in an exemplary embodiment, the prolamin added to the alcohol solvent may be one dissolved in 60-90% alcohol. Also, in an exemplary embodiment, the alcohol solvent to which the insoluble effective substance is added may be 70-95% alcohol. When prolamin and an insoluble effective substance are added to an alcohol, a structure wherein the insoluble effective substance is captured by the prolamin may be formed due to hydrophobic interaction between the insoluble effective substance and the prolamin.

In an exemplary embodiment, the pullulan and the pectin added to the alcohol solution may be pullulan in aqueous phase and pectin in aqueous phase, respectively. Specifically, the pullulan in aqueous phase and the pectin in aqueous phase may be an aqueous pullulan solution and an aqueous pectin solution, more specifically 1-10% aqueous pullulan solution and aqueous pectin solution, respectively.

In an exemplary embodiment, phase separation occurs when the pullulan and the pectin are dissolved respectively in aqueous phases and then added to the alcohol solution in which the prolamin or the prolamin and the insoluble effective substance are dispersed. As a result of the phase separation, the core comprising the prolamin or the prolamin and the insoluble effective substance dispersed in the alcohol is precipitated and, at the same time, a hydrophobic core is formed through self-assembly of the prolamin. A shell structure is formed as the pullulan is coated around the core, and a core-shell particle with pectin surrounding the outermost layer is formed. A Pickering emulsion is formed as the particle is uniformly dispersed stably in the alcohol solution. If the acidity of the solution is adjusted to pH 2.5-6.5, an interconnected network is formed between the pectin of the core-shell particle in the alcohol. In the composition according to an exemplary embodiment of the present disclosure, the interconnected network serves as a support of the core-shell structure, thereby allowing the insoluble effective substance to be captured at high content and allowing the core-shell network structure to maintain the stably dispersed structure for a long time.

In an exemplary embodiment, the method may further comprise a step of gelating the solution with the core-shell network structure formed by adjusting the acidity of the alcohol solution to pH 2.5-6.5. Pectin can be gelated in the presence of acids or sugars. In acidic conditions, hydrogen bonds are formed between the hydroxyl groups of the sugars or ionic bonds with calcium ions are formed. In contrast, depolymerization occurs in basic or weakly acidic conditions. Alternatively, a gelated solution may be prepared when the pectin is comprised in an amount of 2 wt % or more and 3 wt % or less based on the total weight of the composition due to increased viscosity of the solution. The gelation is advantageous that microbial contamination due to osmosis may be prevented.

In an exemplary embodiment, the temperature in the step of obtaining the solution with the core-shell network structure dissolved in the aqueous phase by evaporating the alcohol is not limited. For example, the temperature may be 20-40° C.

The composition according to an exemplary embodiment of the present disclosure may be a cosmetic composition.

In an exemplary embodiment, the cosmetic composition according to the present disclosure may be formulated using a cosmetically or dermatologically acceptable medium or a base. It may be provided as any topically applicable formulation, for example, in the form of a solution, a gel, a solid, an anhydrous paste, an oil-in-water emulsion, a suspension, a microemulsion, a microcapsule, a microgranule, an ionic (liposomal) or non-ionic vesicle, a film, a cream, a lotion, a powder, an ointment, a spray or a concealer stick. In addition, it may be provided in the form of an aerosol composition comprising a foamy or compressed propellant. These compositions may be prepared according to common methods in the art.

In an exemplary embodiment, the cosmetic composition according to the present disclosure may further comprise, in addition to the active ingredient, another ingredient which provides a synergistic effect to the main effect within a range not negatively affecting the main effect. The another ingredient may be easily selected and mixed by those skilled in the art without difficulty depending on the formulation of the cosmetic composition or the purpose of use. Also, in an exemplary embodiment, the cosmetic composition of the present disclosure may further comprise another ingredient commonly used in a cosmetic composition. Examples may comprise a humectant, an emollient, an organic or inorganic pigment, an organic powder, a UV absorbent, an antiseptic, a sterilizer, an antioxidant, a plant extract, a pH-adjusting agent, an alcohol, a colorant, a flavorant, a blood circulation promoter, a cooling agent, an antiperspirant, purified water, etc. The ingredients that may be additionally comprised in the cosmetic composition of the present disclosure are not limited thereto and they may be used within ranges not negatively affecting the purpose and effect of the present disclosure.

The composition according to the present disclosure may be a food composition.

For example, it may be processed into a functional food comprising the active ingredient, such as fermented milk, cheese, yogurt, juice, probiotics, health food, etc., and may be used in the form of various food additives. In an exemplary embodiment, the composition may be a composition for health food. In an exemplary embodiment, the composition for health food may be formulated as a pill, a capsule, a tablet, a granule, a caramel, a drink, etc. In another exemplary embodiment, it may be processed into the form of a liquid, a powder, a granule, a tablet, a tea bag, etc. The composition may be administered by various methods such as simple drinking, administration by injection, spraying, squeezing, etc. The composition may comprise another ingredient that can provide a synergistic effect to the main effect of the present disclosure within a range not negatively affecting the main effect. For example, it may further comprise an additive for improving physical properties, such as a flavorant, a pigment, a sterilizer, an antioxidant, an antiseptic, a humectant, a thickener, a mineral, an emulsifier, a synthetic polymer material, etc. In addition, it may further comprise an auxiliary ingredient such as a water-soluble vitamin, an oil-soluble vitamin, a polypeptide, a polysaccharide, a seaweed extract, etc. These ingredients may be adequately selected and mixed by those skilled in the art depending on the formulation or purpose of use, and the addition amount may be selected within a range not negatively affecting the purpose and effect of the present disclosure. For example, the addition amount of the ingredients may be 0.0001-99.9 wt % based on the total weight of the composition.

The composition according to an exemplary embodiment of the present disclosure may be a pharmaceutical composition. The pharmaceutical composition may further comprise a pharmaceutical adjuvant such as an antiseptic, a stabilizer, a wetting agent, an emulsification accelerator, a salt and/or buffer for control of osmotic pressure, etc. and other therapeutically useful substances.

In an exemplary embodiment, the pharmaceutical composition may be a formulation for oral administration, and the formulation for oral administration may be, for example, a tablet, a pill, a hard or soft capsule, a liquid, a suspension, an emulsion, a syrup, a powder, a dust, a fine granule, a granule, a pellet, etc. These formulations may further comprise, in addition to the active ingredient, a surfactant, a diluent (e.g., lactose, dextrose, sucrose, mannitol, sorbitol, cellulose and glycine), a glidant (e.g., silica, talc, stearic acid and its magnesium or calcium salt and polyethylene glycol). A tablet may further comprise a binder such as magnesium aluminum silicate, starch paste, gelatin, tragacanth, methylcellulose, sodium carboxymethyl cellulose and polyvinylpyrrolidone and, in some cases, may comprise a pharmaceutical additive such as a disintegrant such as starch, agar, alginic acid or its sodium salt, an absorbent, a colorant, a flavorant, a sweetener, etc. The tablet may be prepared by a common mixing, granulation or coating method.

In an exemplary embodiment, the pharmaceutical composition may be a formulation for parenteral administration, and the formulation for parenteral administration may be a formulation for rectal, topical, subcutaneous or transdermal administration. For example, the formulation may be an injection, a medicinal drop, an ointment, a lotion, a gel, a cream, a spray, a suspension, an emulsion, a suppository, a patch, etc., although not being limited thereto.

In an exemplary embodiment, the administration dosage of the pharmaceutical composition will vary depending on the age, sex and body weight of a subject to be treated, the particular disease or pathological condition to be treated, the severity of the disease or pathological condition, administration route and the discretion of a prescriber. The determination of the administration dosage based on these factors is within the level of those skilled in the art. For example, the administration dosage may be 1 mg/kg/day or more or 500 mg/kg/day or more and 1 g/kg/day or less, 500 mg/kg/day or less or 100 mg/kg/day or less. However, the administration dosage does not limit the scope of the present disclosure in any way.

MODE FOR INVENTION

Hereinafter, the present disclosure is described in detail referring to examples, comparative examples and test examples. However, they are merely provided to describe the present disclosure more specifically, and it will be obvious to those having ordinary knowledge in the art that the scope of the present disclosure is not limited by the examples, comparative examples and test examples.

Example 1

A composition comprising a core-shell network structure according to an exemplary embodiment of the present disclosure was prepared as follows.

0.5 wt % of zein in powder form based on the total weight of a composition was added to a 70% alcohol aqueous solution and then dispersed by stirring. Then, 0.5 wt % of pullulan based on the total weight of the composition, which was dissolved in an aqueous phase of pH 7 or lower, was added at room temperature to the alcohol solution in a drop-by-drop manner and then dissolved by stirring. Then, 0.5 wt % pectin in aqueous phase based on the total weight of the composition was added to the solution. Finally, a core-shell network solution was obtained by evaporating the alcohol from the solution with an evaporator.

Example 2

A core-shell network structure composition in which an insoluble effective substance is captured was prepared as an exemplary embodiment of the present disclosure.

0.5 wt % of zein in powder form based on the total weight of a composition was added to a 70% alcohol aqueous solution and then dispersed by stirring. Then, 1 wt % of red ginseng saponin (BioGF1K Complex™, Amorepacific) based on the total weight of the composition was added to the solution as an insoluble effective substance and then dispersed by stirring enough such that hydrophobic interaction occurred between the zein and the effective substance. Then, 0.5 wt % of pullulan based on the total weight of the composition, which was dissolved in an aqueous phase of pH 7 or lower, was added at room temperature and then dissolved by stirring. Then, 0.5 wt % pectin in aqueous phase based on the total weight of the composition was added to the solution. Finally, a core-shell network solution was obtained by evaporating the alcohol from the solution with an evaporator.

Comparative Example 1

A composition not comprising a network structure was prepared as a comparative example of the present disclosure.

0.5 wt % of zein in powder form based on the total weight of a composition was added to a 70% alcohol aqueous solution and then dispersed by stirring. Then, 0.5 wt % of pullulan based on the total weight of the composition, which was dissolved in an aqueous phase of pH 7 or lower, was added at room temperature to the alcohol solution in a drop-by-drop manner and then dissolved by stirring. Finally, a core-shell solution was obtained by evaporating the alcohol from the solution with an evaporator.

Comparative Example 2

A composition not comprising a network structure in which an insoluble effective substance is captured was prepared as a comparative example of the present disclosure.

0.5 wt % of zein in powder form based on the total weight of a composition was added to a 70% alcohol aqueous solution and then dispersed by stirring. Then, 1 wt % of red ginseng saponin (BioGF1K Complex™, Amorepacific) based on the total weight of the composition was added to the solution as an insoluble effective substance and then dispersed by stirring enough such that hydrophobic interaction occurred between the zein and the effective substance. Then, 0.5 wt % of pullulan based on the total weight of the composition, which was dissolved in an aqueous phase of pH 7 or lower, was added at room temperature and then dissolved by stirring. Finally, a core-shell solution was obtained by evaporating the alcohol from the solution with an evaporator.

[Test Example 1] Investigation of Particle Size and Distribution

Figure 2:
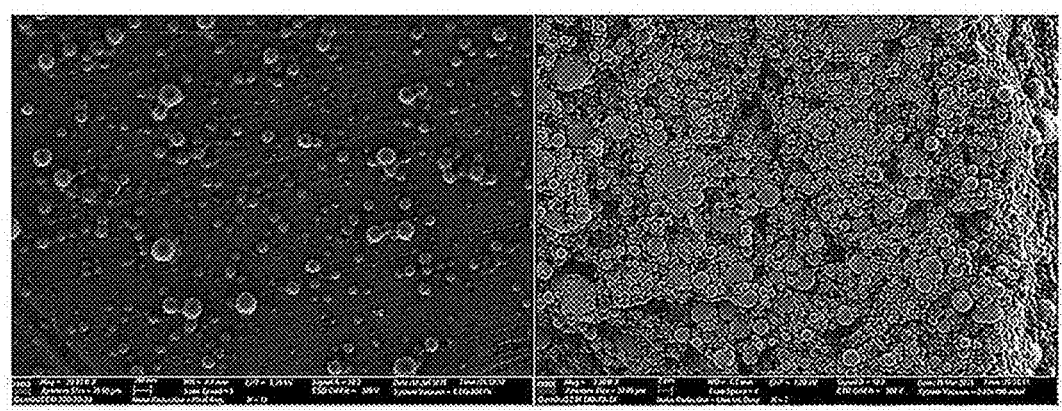
FIG. 2 shows the electron microscopic images of a comparative example of the present disclosure with no core-shell network formed (left: not comprising insoluble effective substance, right: comprising insoluble effective substance).

The core-shell structures formed in the compositions of Comparative Example 1, Comparative Example 2, Example 1 and Example 2 were identified by scanning electron microscopy (SEM). The result is shown in FIG. 2 and FIG. 3.

For Comparative Example 1, although a core-shell structure was formed, the particles of the structure were separated from each other. For Comparative Example 2 wherein the insoluble effective substance was captured, the structure was disrupted and the particles were aggregated with each other (FIG. 2).

In contrast, for Example 1, a web-like network was formed between the core-shell structures and the particles were uniformly distributed in the solution. For Example 2 wherein the insoluble effective substance was captured, particles with a size of 200-500 nm were connected by an interconnected network and dispersed uniformly with regular intervals (FIG. 3).

Figure 3:
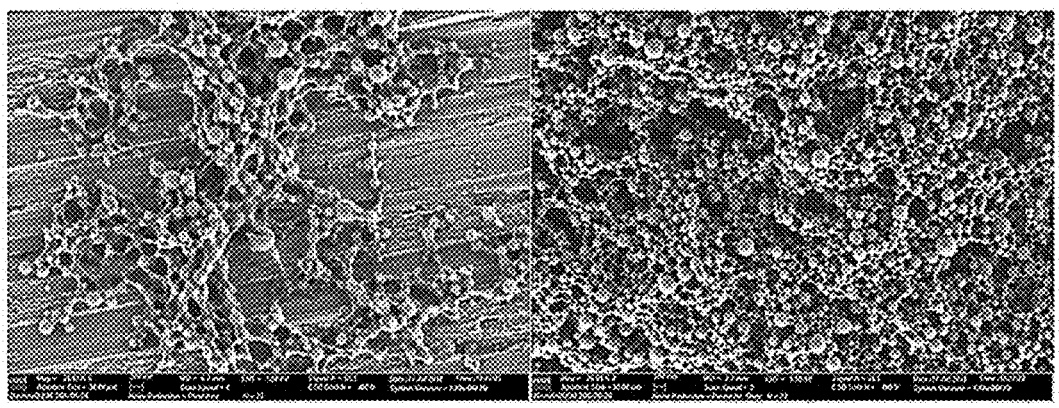
FIG. 3 shows the electron microscopic images showing the formation of a core-shell network structure according to an example of the present disclosure (left: not comprising insoluble effective substance, right: comprising insoluble effective substance).
Figure 4:
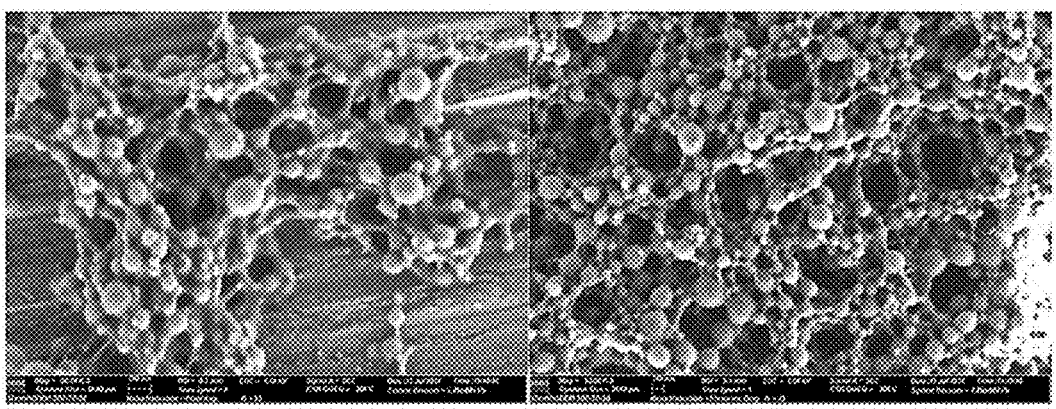
FIG. 4 shows the magnified electron microscopic images showing the formation of a core-shell network structure according to an example of the present disclosure (left: not comprising insoluble effective substance, right: comprising insoluble effective substance).

FIG. 4 magnifies the structure in the solution of FIG. 3. It was confirmed that, for the examples of the present disclosure, core-shell structures with a size of hundreds of nanometers were formed and the particles were distributed densely and uniformly as being connected by an interconnected network.

Figure 5:
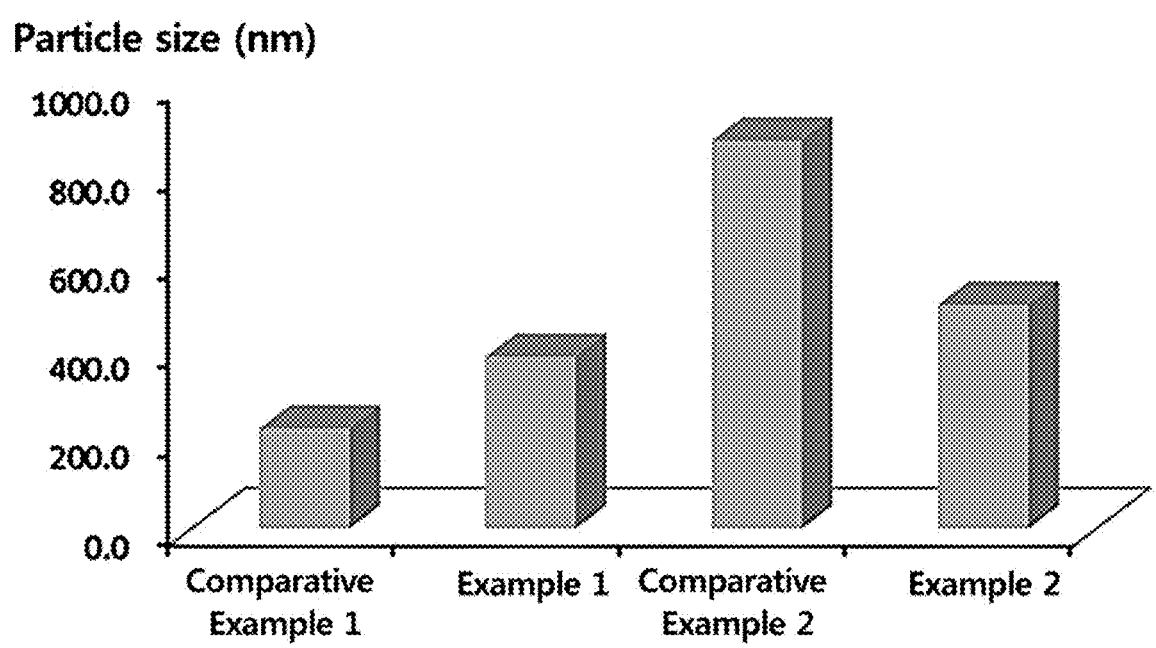
FIG. 5 shows a result of measuring the size of core-shell particles in compositions according to examples and comparative examples of the present disclosure.

FIG. 5 shows a result of measuring the hydrodynamic average particle size of the particles formed in the solutions of Comparative Examples 1-2 and Examples 1-2 using Marven's dynamic light scattering device. For Comparative Example 2, wherein the interconnected network was not formed between the core-shell particles, the particle was increased about 4 times or larger as compared to Comparative Example 1 when the insoluble effective substance was captured. In contrast, for Example 2, the particle size was not increased greatly after the capturing of the insoluble effective substance, with about 500 nm or smaller. This suggests that the structure of the core-shell particles of the present disclosure is maintained stably as they are connected by the interconnected network.

[Test Example 2] Evaluation of Formulation Stability

The formulation stability of the compositions of Example 1 and Example 2 was investigated while storing them under harsh conditions (hot and cold cycles of room temperature, 4° C. and 60° C.) for a total of 4 weeks.

Figure 6:
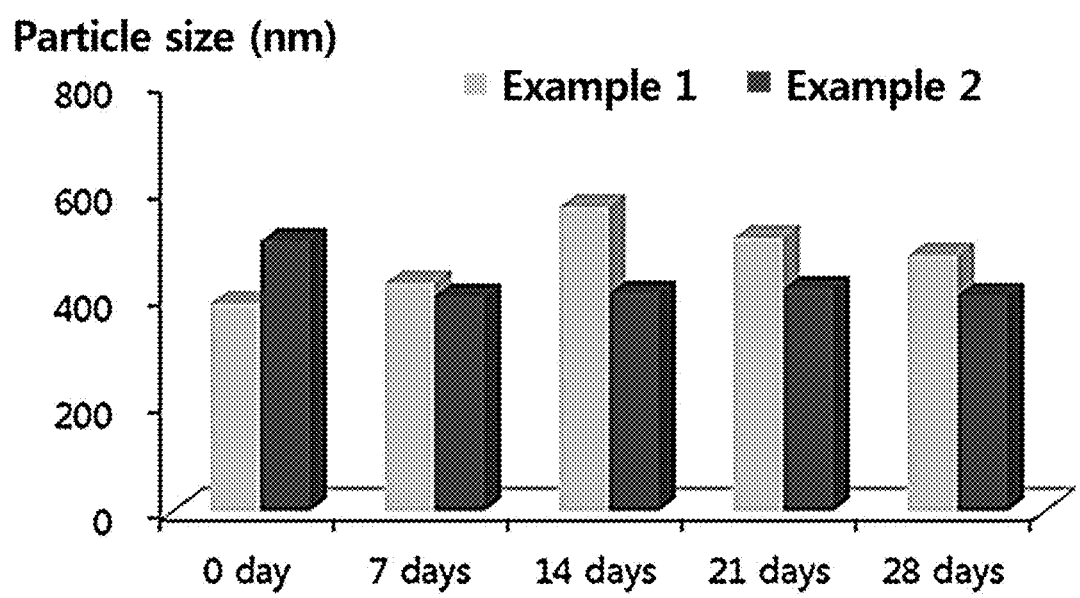
FIG. 6 shows that a formulation (particle size) of a composition is maintained stably for a long time as a core-shell network structure is formed in examples of the present disclosure.
Figure 7A:
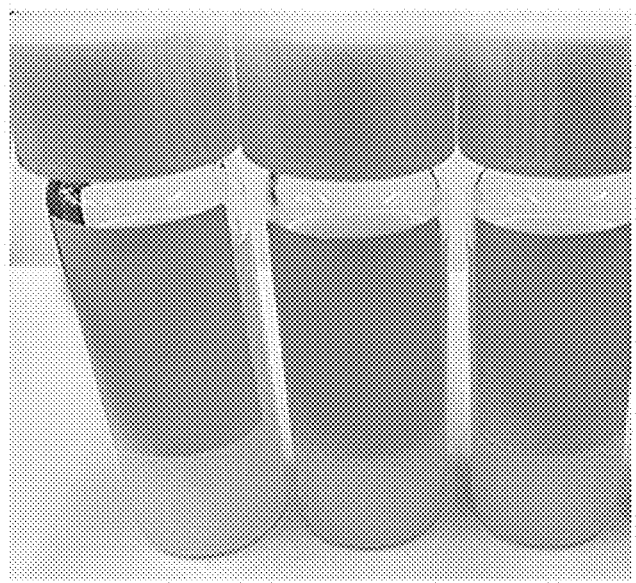
FIG. 7A shows a photograph of compositions comprising a core-shell network structure according to an example of the present disclosure taken on the day of preparation.
Figure 7B:
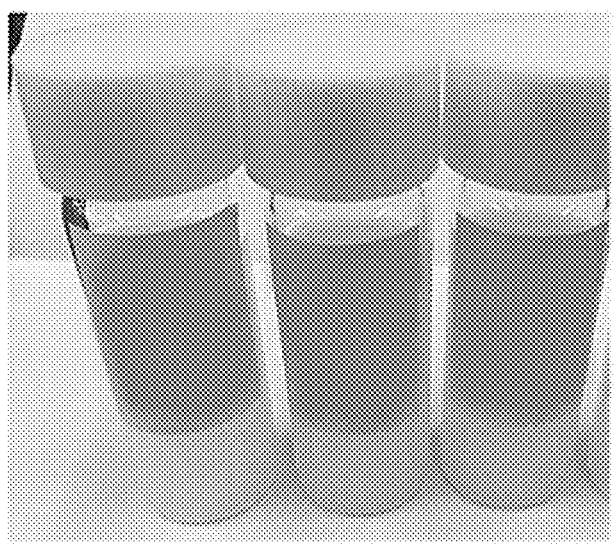
FIG. 7B shows a photograph of compositions comprising a core-shell network structure according to an example of the present disclosure and an effective substance taken on the day of preparation.
Figure 7C:
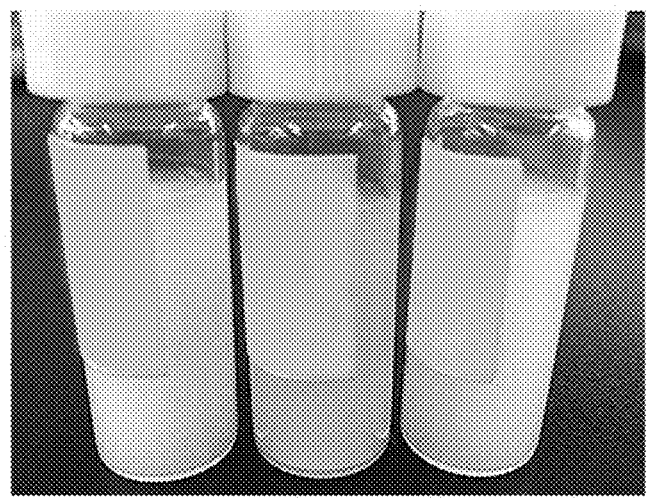
FIG. 7C shows that a formulation of compositions comprising a core-shell network structure according to an example of the present disclosure is maintained stably for a long time.
Figure 7D:
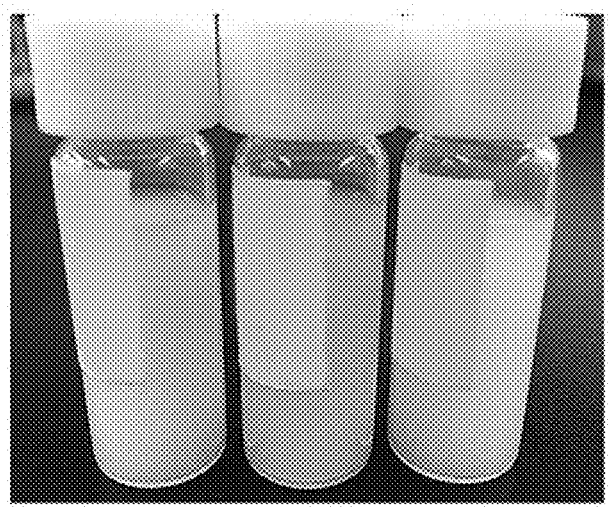
FIG. 7D shows that a formulation of compositions comprising a core-shell network structure and an effective substance according to an example of the present disclosure is maintained stably for a long time.

FIG. 6 shows a result of measuring the change in the size of core-shell particles in each composition with the lapse of time. It can be seen that the composition according to the present disclosure maintained the particle size at 500 nm or smaller either when the insoluble effective substance was not captured (Example 1) or captured (Example 2). When the insoluble effective substance was captured in the core (Example 2), the size was maintained at an average of 400 nm or smaller. For Example 1, wherein the composition comprised only the core-shell network structure without the insoluble effective substance, the particle size was maintained at about 500 nm. FIGS. 7A-7D show a result of investigating the dispersion stability of the formulation on the day of preparation and 4 weeks later. It was confirmed that dispersion stability was maintained without precipitation even after storage for 4 weeks under harsh conditions for both Examples 1 and 2.

Example 2 showed formation of sphere-like core-shell particles and interconnected network structure as compared to the control group. It seems that the core formed through the hydrophobic interaction between the prolamin and the insoluble effective substance undergoes phase separation and, at the same time, the particle itself serves as a surfactant that maintains interfacial stability and the pectin serves as a basis for formation of the chain-like network. That is to say, as the solution comprising the core-shell particle turns into a Pickering emulsion, the pectin forms the chain-like network in the presence of the alcohol, thereby strengthening physical interfacial stability.

[Test Example 3] Evaluation of Effect on Skin Cell Proliferation

The cytotoxicity of Examples 1 and 2 on skin cells was investigated. Specifically, after adding 10 μL of a CCK-8 reagent to normal human fibroblasts (purchased from GIBCO) which were being cultured on a 96-well plate and keeping at 37° C. for 2 hours, absorbance was measured at 450 nm. The medium in which the cells were cultured was treated with the solution of Example 1 or 2 at 2 ppm (0.0002 wt %). That is to say, the administration dosage of the administered core-shell network structure was 2 mg/kg. Cell viability was represented by the percentage (%) of the absolute optical density of each sample with respect to an untreated sample.

Figure 8:
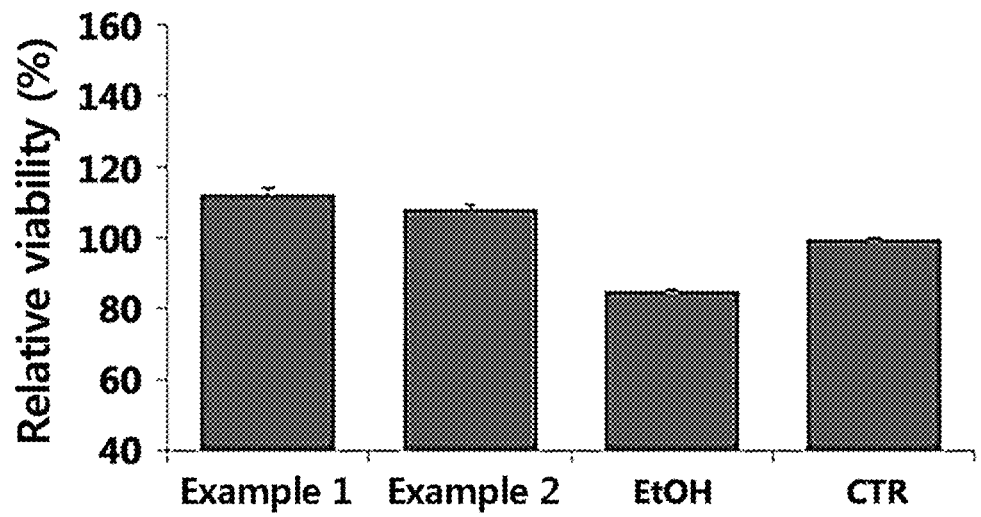
FIG. 8 shows a result of evaluating the viability of cells treated with core-shell network structures according examples of the present disclosure.
Figure 9:
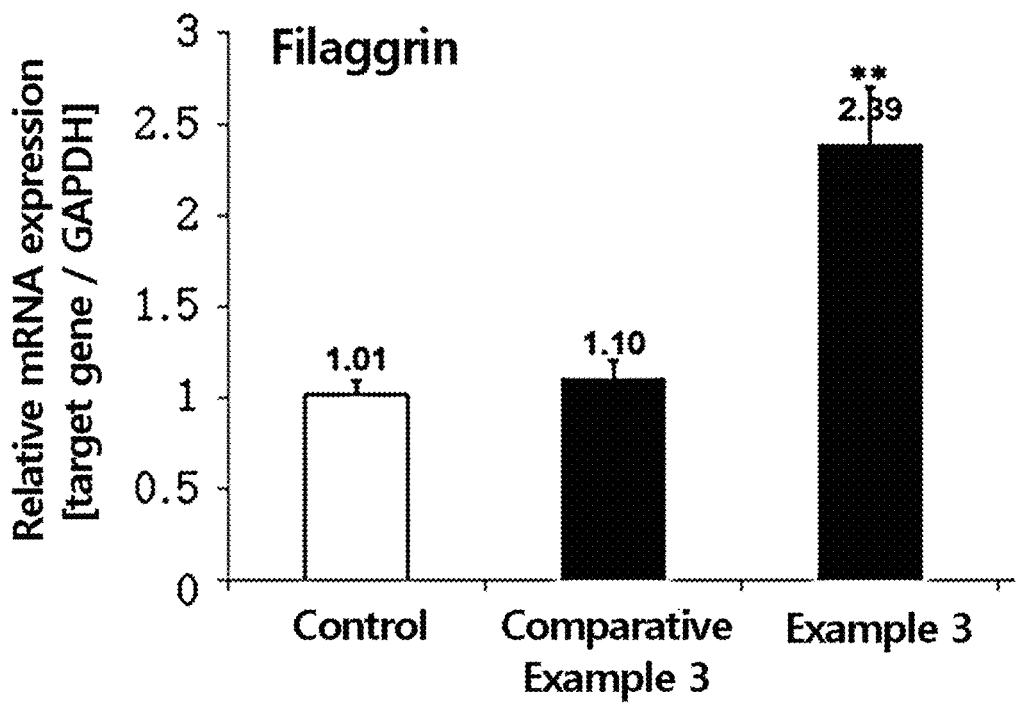
FIG. 9 shows a result of analyzing the expression level of filaggrin, which is a skin moisturization barrier marker, in order to investigate the moisturization effect of a core-shell network structure according to an example of the present disclosure.
Figure 10:
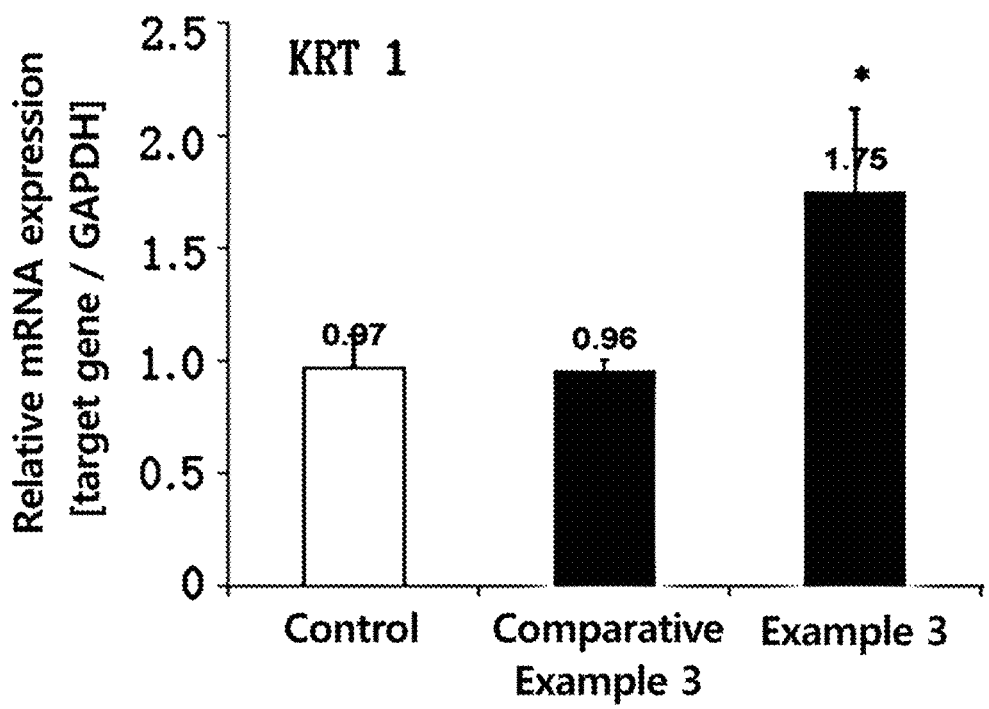
FIG. 10 shows a result of analyzing the expression level of KRT 1, which is a skin moisturization barrier marker, in order to investigate the moisturization effect of a core-shell network structure according to an example of the present disclosure.
Figure 11:
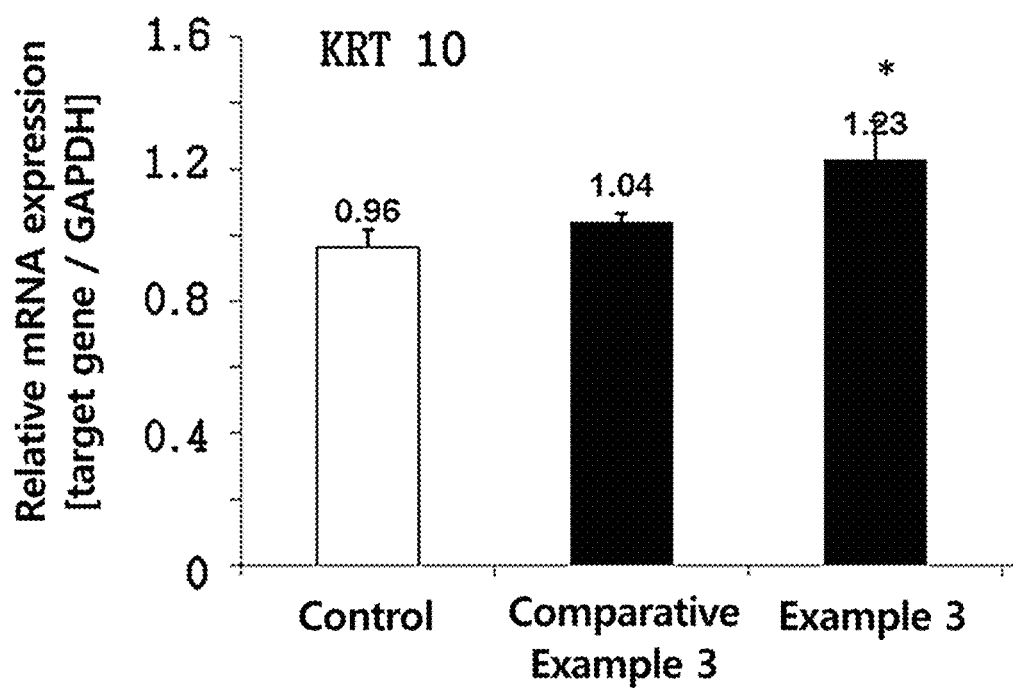
FIG. 11 shows a result of analyzing the expression level of KRT 10, which is a skin moisturization barrier marker, in order to investigate the moisturization effect of a core-shell network structure according to an example of the present disclosure.
Figure 12:
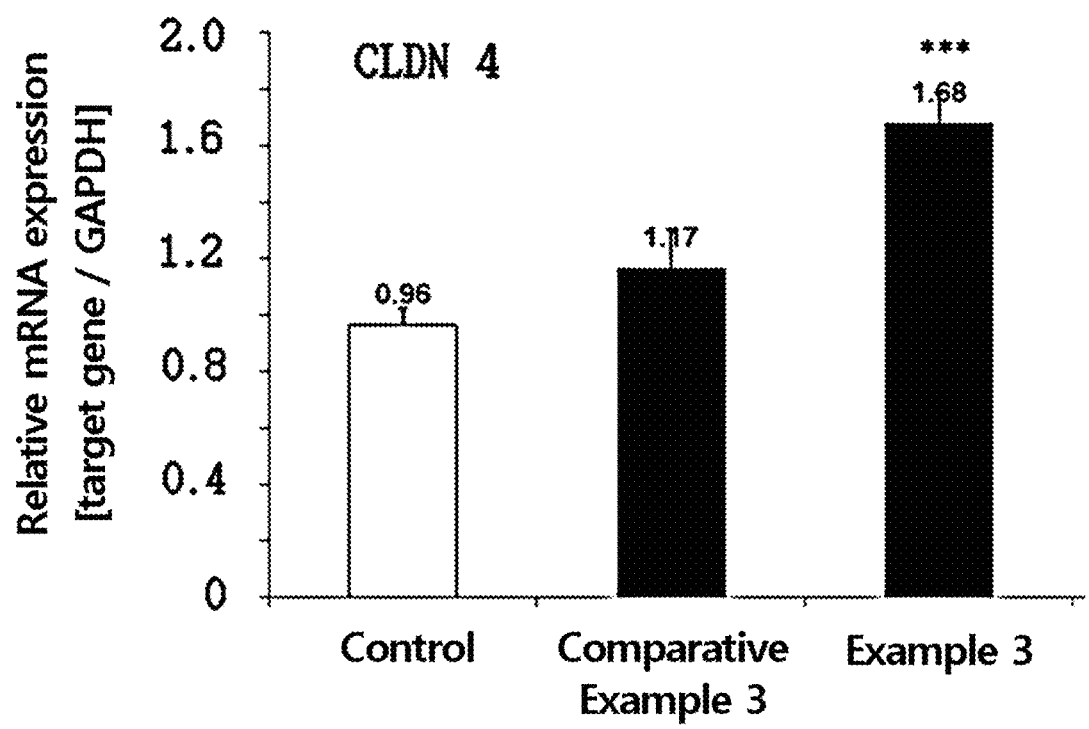
FIG. 12 shows a result of analyzing the expression level of CLDN 4, which is a skin moisturization barrier marker, in order to investigate the moisturization effect of a core-shell network structure according to an example of the present disclosure.
Figure 13:
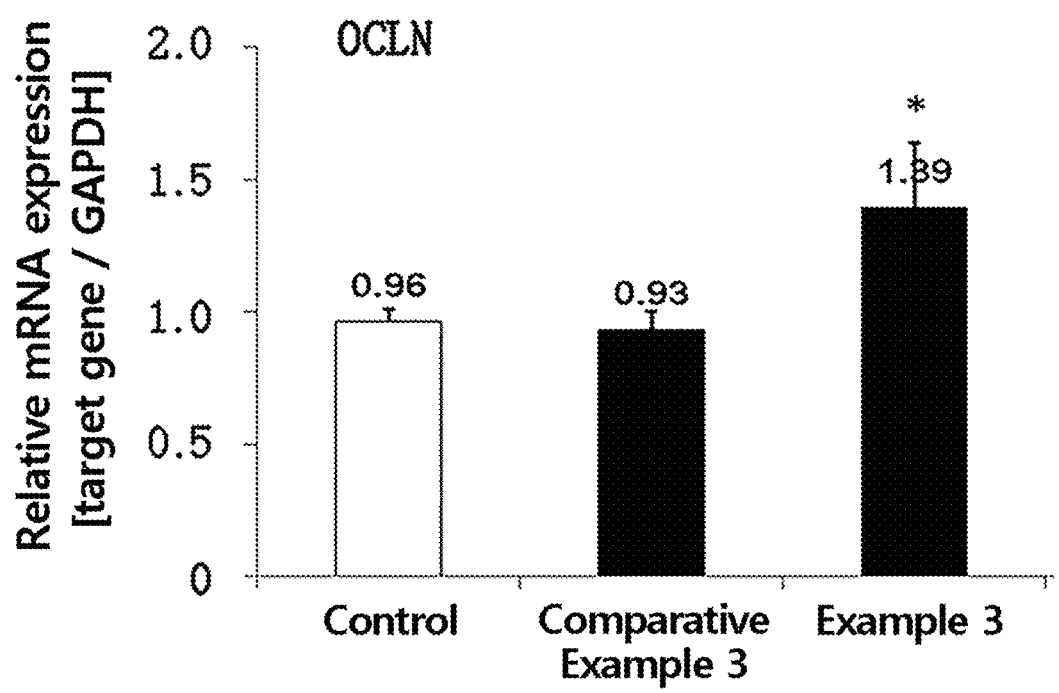
FIG. 13 shows a result of analyzing the expression level of OCLN, which is a skin moisturization barrier marker, in order to investigate the moisturization effect of a core-shell network structure according to an example of the present disclosure.

As a result of the CCK8 cytotoxicity test, cell proliferation was promoted in both Example 1 and Example 2 (comprising the insoluble effective substance) as compared to the untreated (control) group, as shown in FIG. 8. This means that the composition according to the present disclosure can provide skin barrier-enhancing effect.

Example 3

A composition comprising a core-shell network structure according to an exemplary embodiment of the present disclosure was prepared as follows.

0.025% of zein in powder form based on the total weight of a composition was added to a 70% alcohol aqueous solution and then dispersed by stirring. Then, 0.05 wt % of pullulan based on the total weight of the composition, which was dissolved in an aqueous phase of pH 7 or lower, was added at room temperature to the alcohol solution in a drop-by-drop manner and then dissolved by stirring. Then, 0.125 wt % pectin in aqueous phase based on the total weight of the composition was added to the solution. Finally, a core-shell network solution was obtained by evaporating the alcohol from the solution with an evaporator.

Comparative Example 3

A composition not comprising a network structure was prepared as a comparative example of the present disclosure.

0.025 wt % of zein in powder form based on the total weight of a composition was added to a 70% alcohol aqueous solution and then dispersed by stirring. Then, 0.05 wt % of pullulan based on the total weight of the composition, which was dissolved in an aqueous phase of pH 7 or lower, was added at room temperature to the alcohol solution in a drop-by-drop manner and then dissolved by stirring. Finally, a core-shell solution was obtained by evaporating the alcohol from the solution with an evaporator.

[Test Example 4] Evaluation of Skin-Moisturizing Effect

The skin-moisturizing effect of the composition comprising the core-shell network structure according to an exemplary embodiment of the present disclosure was investigated as follows.

After seeding human hair follicular keratinocytes (purchased from ATCC) onto a 6-well plate, with $3\times10^5$ cells/well, and culturing for 24 hours, the cells were treated with Example 3 or Comparative Example 3 and then cultured further for 24 hours. Then, after extracting RNA using Invitrogen's TRIZol reagent, cDNA was synthesized using Invitrogen's Superscript III®. The mRNA expression level of the genes filaggrin (NCBI Reference Sequence of *Homo sapiens* filaggrin mRNA: NM_002016.2), KRT 1 (NCBI Reference Sequence of *Homo sapiens* keratin 1 mRNA: NM_006121.4), KRT 10 (NCBI Reference Sequence of *Homo sapiens* keratin 10 mRNA: NM_000421.4), CLDN 4 (NCBI Reference Sequence of *Homo sapiens* claudin 4 mRNA: NM_001305.4) and OCLN (vReference Sequence of *Homo sapiens* occludin transcript variant 1 mRNA: NM_002538.4), which are known as skin moisturization factors, was analyzed by conducing quantitative polymerase chain reaction (qPCR) using specific primers of the each skin moisturization factors and a TaqMan gene expression assay tool using KGF (keratinocyte growth factor) and VEGF (vascular endothelial growth factor) growth factors.

As shown in FIGS. 9-13, the gene expression levels of the skin moisturization factors were increased in the group treated with the core-shell network composition (Ecoweb) of Example 3 as compared to the untreated group (control). The increase was remarkably significant as compared to Comparative Example 3 without comprising the network structure.

[Test Example 5] Evaluation of Skin-Regenerating Effect

The skin-regenerating effect of the composition comprising the core-shell network structure according to an exemplary embodiment of the present disclosure was investigated as follows.

First, human keratinocytes (HaCaT) purchased from CLS (Cat No. 300493) were seeded onto a 24-well cell culture plate at a concentration of $2.0\times10^5$ cells/600 μL, in DMEM (Lonza, #12-604F) containing 10% fetal bovine serum (GIBCO, #16000-044) and antibiotics (Lonza, #17-602E). After culturing in a 5% $CO_2$ incubator at 37° C. for 24 hours and replacing the medium with DMEM containing 1% fetal bovine serum, the cells were cultured further for 16 hours. After the cells were filled on the culture plate, the cells were damaged by applying a linear scratch using a scratcher (SPL, #SPL201925) and then washed twice. Core-shell network solutions comprising 0.005 wt %, 0.25 wt %, 0.5 wt % or 1 wt % of the core-shell network structure based on the total weight of the solution, were prepared in the same manner as in Example 3 (Examples 4-7). The DMEM (containing 1% fetal bovine serum) containing the damaged cells was treated with the core-shell network solutions of Examples 4-7 at 0.000001 wt %, 0.000005 wt %, 0.0001 wt % or 0.0002 wt %. That is to say, the administration dosage of the administered core-shell network structure was 1, 5, 100 or 200 mg/kg.

An untreated group not treated with the core-shell network structure was used as a negative control group, and a positive control group was treated with 20 µM madecassoside (Sigma Aldrich, M6949, madecassoside from *Centella asiatica*) which is known to have superior skin-regenerating effect.

The negative control group, the positive control group and the groups treated with the core-shell network structure at different concentrations were placed on a time-lapse microscope (JuLI™ Stage, NanoEnT) stage in a $CO_2$ incubator and each well was imaged for 48 hours with 1-hour intervals. Then, wound healing area (%) was determined from the acquired images using a software analysis tool (Wound Healing tool).

Figure 14:
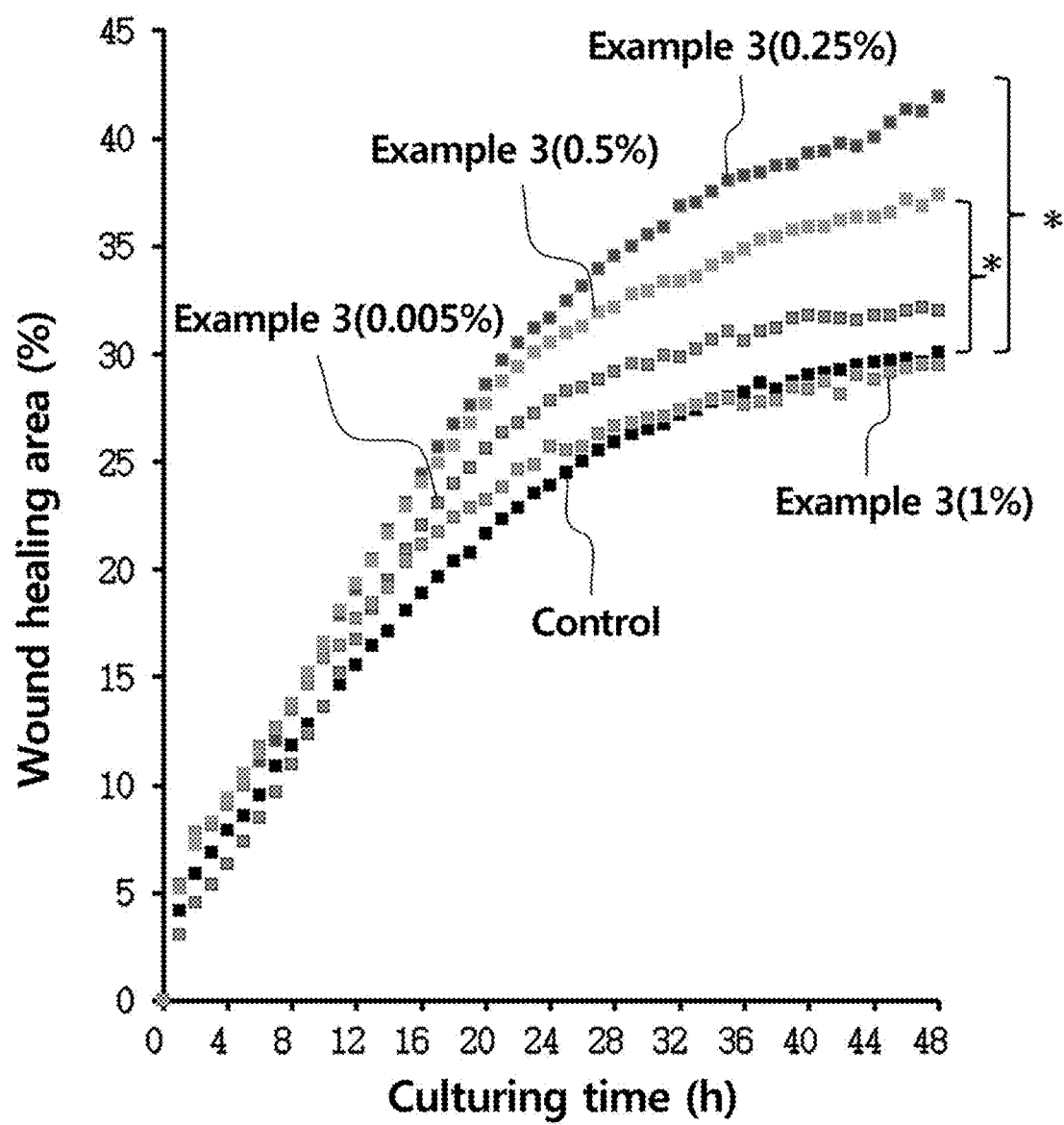
FIG. 14 shows a result of analyzing the degree of skin regeneration by a core-shell network structure according to an example of the present disclosure at different concentrations.

As shown in FIG. 14, the group treated with 0.25 wt % core-shell network structure showed the most superior skin-regenerating effect. The group treated with 1 wt % showed slightly better regenerating effect than the untreated negative control group until about 24 hours. But, after 48 hours, the degree of skin regeneration was similar to that of the untreated negative control group. This may be due to the interaction owing to the strong negative charge of the pectin which forms a network in the core-shell network structure.

Figure 15:
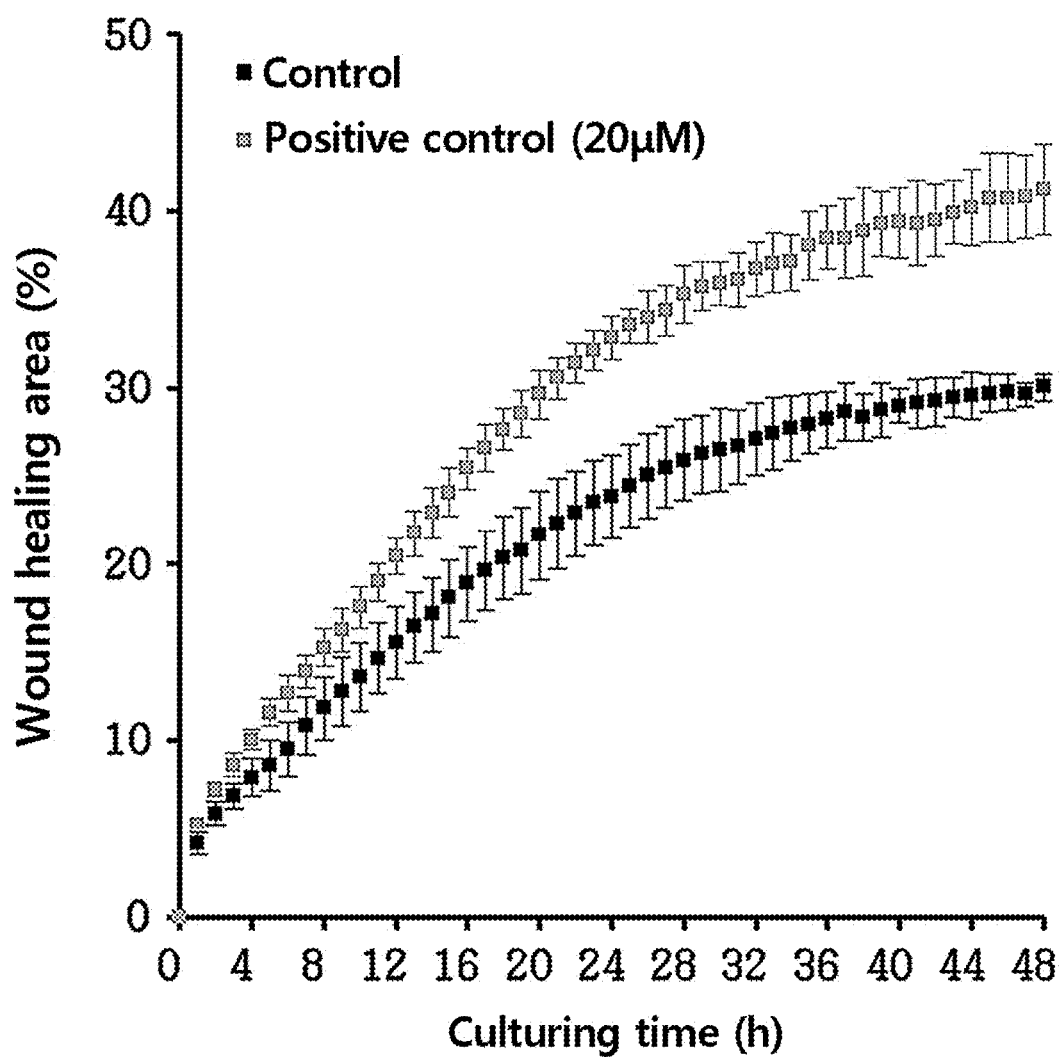
FIG. 15 shows a result of analyzing the degree of skin regeneration by madecassoside as a positive control group.
Figure 16:
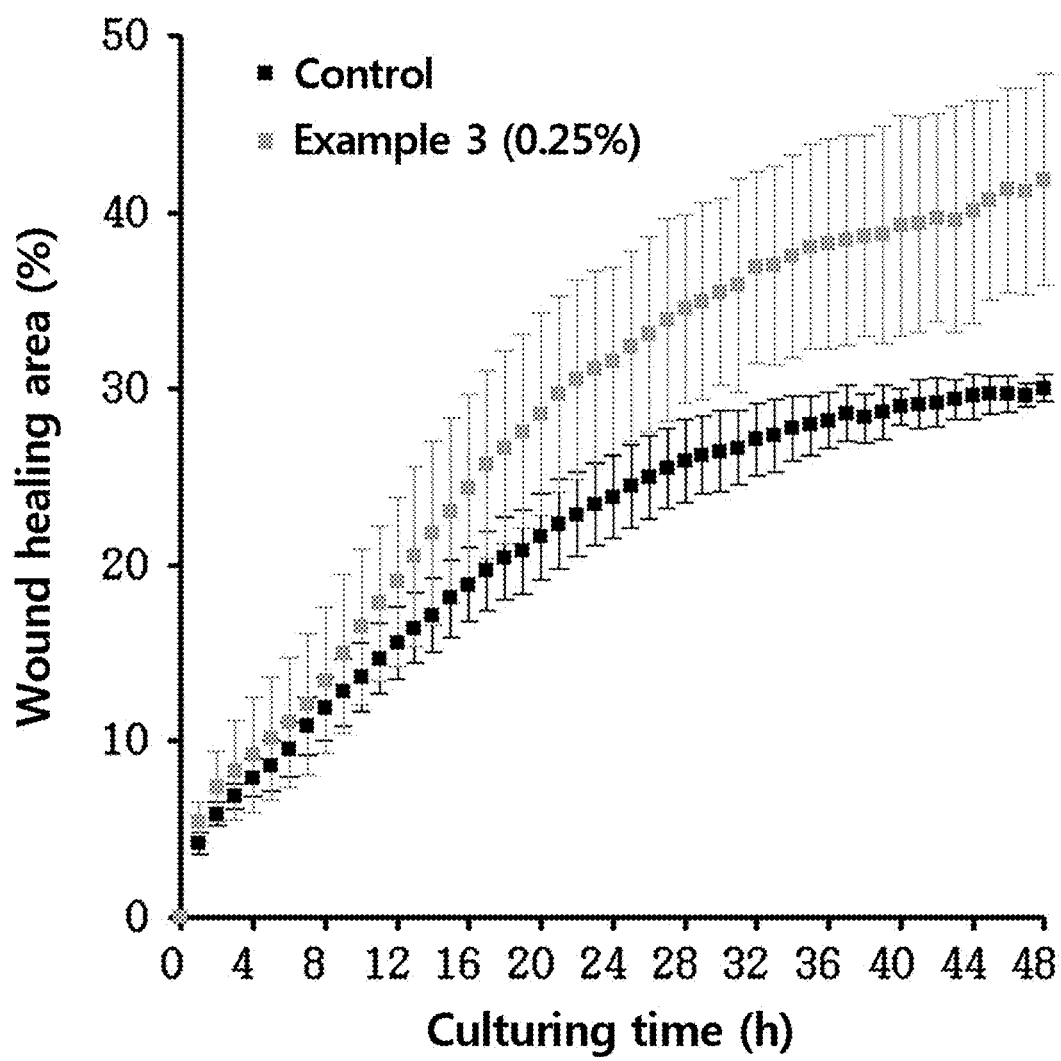
FIG. 16 shows a result of analyzing the degree of skin regeneration by a core-shell network structure according to an example of the present disclosure at a concentration of 0.25 wt % based on the total weight of a composition.
Figure 17:
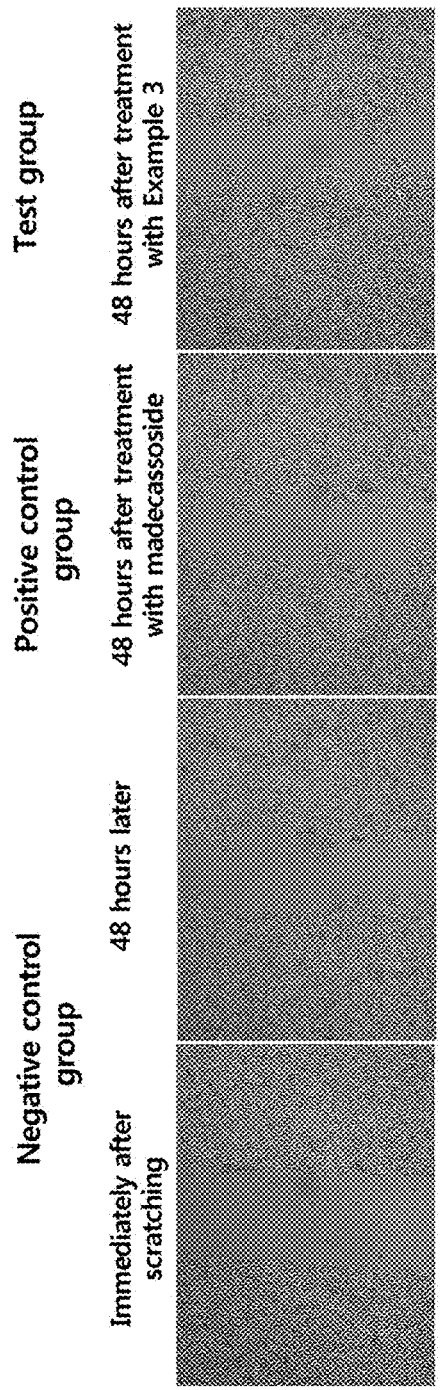
FIG. 17 shows compares the images of skin cells treated with a core-shell network structure according to an example of the present disclosure, untreated skin cells as a negative control group and skin cells treated with madecassoside as a positive control group.

As can be seen from FIGS. 14-16, the wound healing area after 48 hours was 30.06% for the negative control group (control), 41.25% (1.37 times as compared to the control group) for the positive control group (20 µM madecassoside), and 41.88% (1.39 times as compared to the negative control group) for 0.25 wt % core-shell network structure. FIG. 17 shows the microscopic images from which the wound healing area values of FIG. 15 and FIG. 16 were calculated. The wound healing area was 32.03% for 0.005 wt % core-shell network structure (1.06 times as compared to the negative control group), and 37.35% (1.24 times as compared to the negative control group) for 0.5 wt % core-shell network structure. This means that the core-shell network structure according to an exemplary embodiment of the present disclosure has superior skin-regenerating effect.

The present disclosure may provide the following exemplary embodiments.

A first exemplary embodiment may provide a core-shell network structure comprising a core-shell particle formed of: a core comprising prolamin; and a shell comprising pullulan and pectin, wherein an interconnected network is formed between the core-shell particles as the pullulan surrounds the core and the pectin is located at an outermost layer of the shell.

A second exemplary embodiment may provide the core-shell network structure according to the first exemplary embodiment, wherein the prolamin comprises one or more selected from a group consisting of zein, hordein, secalin, kafirin, gliadin, oryzin and avenin.

A third exemplary embodiment may provide the core-shell network structure according to the first exemplary embodiment or the second exemplary embodiment, wherein the structure comprises: 0.025-7.5 wt % of prolamin; 0.025-12.5 wt % of pullulan; and 0.05-10 wt % of pectin, based on the total weight of the structure.

A fourth exemplary embodiment may provide the core-shell network structure according to any of the first to third exemplary embodiments, wherein the core-shell particle has an average particle size of greater than 100 nm and 600 nm or smaller.

A fifth exemplary embodiment may provide a composition for solubilizing an insoluble effective substance, which comprises one or more structure according to any of the first to fourth exemplary embodiments.

A sixth exemplary embodiment may provide the composition for solubilizing according to any of the first to the fifth exemplary embodiment, wherein the insoluble effective substance is a hydrophobic and alcohol-soluble substance.

A seventh exemplary embodiment may provide a composition for one or more of skin barrier enhancement, skin moisturization and skin regeneration, which comprises one or more structure according to any of the first to fourth exemplary embodiments as an active ingredient.

An eighth exemplary embodiment may provide the composition according to any of the first to the seventh exemplary embodiment, wherein the active ingredient is comprised in an amount of 0.005 wt % or more and less than 1 wt % based on the total weight of the composition.

A ninth exemplary embodiment may provide the composition according to any of the first to the eighth exemplary embodiment, wherein an administration dosage of the active ingredient is 1-500 mg/kg/day.

A tenth exemplary embodiment may provide a composition comprising one or more structure according to the first to ninth exemplary embodiments, which further comprises an insoluble effective substance in the core of the structure, wherein the insoluble effective substance is captured by the prolamin of the core.

An eleventh exemplary embodiment may provide the composition according to any of the first to the tenth exemplary embodiment, wherein the insoluble effective substance is a hydrophobic and alcohol-soluble substance.

A twelfth exemplary embodiment may provide the composition according to any of the first to the eleventh exemplary embodiment, wherein the prolamin of the core forms a brick-like structure around the insoluble effective substance.

A thirteenth exemplary embodiment may provide the composition according to any of the first to the twelfth exemplary embodiment, wherein the insoluble effective substance comprises: a triterpenoid comprising one or more selected from a group consisting of oleanolic acid, ursolic acid and arjunolic acid; a polyphenol or a polyphenol derivative comprising one or more selected from a group consisting of amentoflavone, ellagic acid, apigenin, bergenin, diosmetin, univestin, resveratrol, isoflavone and catechin; an oily fatty acid comprising one or more selected from a group consisting of salicylic acid, α-lipoic acid, caffeine, tocopherol, docosahexaenoic acid (DHA), eicosapentaenoic acid (EPA) and conjugated linolenic acid (CLA); a sphingolipid comprising one or more selected from a group consisting of sphingomyelin, ganglioside, cerebroside, ceramide, glycosyl ceramide, lactosyl ceramide, galactosyl ceramide and xylosyl ceramide; a saponin comprising compound K (20-O-β-D-glucopyranosyl-20(S)-protopanaxadiol); carotene or a carotene derivative; and a natural extract comprising one or more selected from a group consisting of ginkgo leaf extract and red ginseng extract.

A fourteenth exemplary embodiment may provide the composition according to any of the first to the thirteenth exemplary embodiment, wherein the composition comprises: 0.01-3 wt % of prolamin; 0.01-5 wt % of pullulan; and 0.01-2 wt % of pectin, based on the total weight of the composition.

A fifteenth exemplary embodiment may provide the composition according to any of the first to the fourteenth exemplary embodiment, wherein the insoluble effective substance is comprised in an amount of 0.01-10 wt % based on the total weight of the composition.

A sixteenth exemplary embodiment may provide the composition according to any of the first to the fifteenth exemplary embodiment, wherein the composition is for one or more of skin barrier enhancement, skin moisturization and skin regeneration.

A seventeenth exemplary embodiment may provide the composition according to any of the first to the sixteenth exemplary embodiment, wherein the composition is a cosmetic composition.

An eighteenth exemplary embodiment may provide a method for preparing the structure according to any of the first to seventeenth exemplary embodiments, which comprises: a step of forming a core by dispersing prolamin in an alcohol solvent; a step of forming a shell surrounding the core by adding pullulan onto the alcohol solution in a drop-by-drop manner; a step of coating pectin on an outermost layer of the shell and forming a network between the shell by adding pectin to the pullulan-added alcohol solution; and a step of obtaining a solution with a core-shell network structure dissolved in an aqueous phase formed by evaporating the alcohol from the pectin-added solution.

A nineteenth exemplary embodiment may provide a method for preparing the composition according to any of the first to the eighteenth exemplary embodiment, which comprises: a step of forming a core by dispersing prolamin and an insoluble effective substance in an alcohol solvent; a step of forming a shell surrounding the core by adding pullulan onto the alcohol solution in a drop-by-drop manner; a step of coating pectin on an outermost layer of the shell and forming a network between the shells by adding pectin to the pullulan-added alcohol solution; and a step of obtaining a solution with a core-shell network structure dissolved in an aqueous phase by evaporating the alcohol from the pectin-added solution.

A twentieth exemplary embodiment may provide the preparation method according to any of the first to the nineteenth exemplary embodiment, wherein the step of forming the network between the shells further comprises a step of gelating the solution with the core-shell network structure formed by adjusting the acidity of the alcohol solution to pH 2.5-6.5.

A twenty-first exemplary embodiment may provide the preparation method according to any of the first to the twentieth exemplary embodiment, wherein the temperature in the step of evaporating the alcohol is 20-40° C.

The invention claimed is:

1. A core-shell network structure comprising a core-shell particle formed of:
a core comprising prolamin; and
a shell comprising pullulan and pectin,
wherein an interconnected network is formed between the core-shell particles as the pullulan surrounds the core and the pectin is located at an outermost layer of the shell.

2. The core-shell network structure according to claim 1, wherein the prolamin comprises one or more selected from a group consisting of zein, hordein, secalin, kafirin, gliadin, oryzin and avenin.

3. The core-shell network structure according to claim 1, wherein the structure comprises:
0.025-7.5 wt % of prolamin;
0.025-12.5 wt % of pullulan; and
0.05-10 wt % of pectin,
based on the total weight of the structure.

4. The core-shell network structure according to claim 1, wherein the core-shell particle has an average particle size of greater than 100 nm and 600 nm or smaller.

5. A method for one or more of skin barrier enhancement, skin moisturization and skin regeneration, which comprises administering an effective amount of the structure according to claim 1 to a subject in need thereof.

6. The method according to claim 5, wherein the structure is comprised in a composition as an active ingredient,
wherein the composition comprises the structure in an amount of 0.005 wt % or more and less than 1 wt % based on the total weight of the composition.

7. The method according to claim 5, wherein an administration dosage of structure is 1-500 mg/kg/day.

8. A composition comprising the structure according to claim 1,
which further comprises an insoluble effective substance in the core of the structure,
wherein the insoluble effective substance is captured by the prolamin of the core.

9. The composition according to claim 8, wherein the insoluble effective substance is a hydrophobic and alcohol-soluble substance.

10. The composition according to claim 8, wherein the prolamin of the core forms a brick-like structure around the insoluble effective substance.

11. The composition according to claim 8, wherein the insoluble effective substance comprises: a triterpenoid comprising one or more selected from a group consisting of oleanolic acid, ursolic acid and arjunolic acid; a polyphenol or a polyphenol derivative comprising one or more selected from a group consisting of amentoflavone, ellagic acid, apigenin, bergenin, diosmetin, univestin, resveratrol, isoflavone and catechin; an oily fatty acid comprising one or more selected from a group consisting of salicylic acid, α-lipoic acid, caffeine, tocopherol, docosahexaenoic acid (DHA), eicosapentaenoic acid (EPA) and conjugated linolenic acid (CLA); a sphingolipid comprising one or more selected from a group consisting of sphingomyelin, ganglioside, cerebroside, ceramide, glycosyl ceramide, lactosyl ceramide, galactosyl ceramide and xylosyl ceramide; a saponin comprising compound K (20-O-β-D-glucopyranosyl-20(S)-protopanaxadiol); carotene or a carotene derivative; and a natural extract comprising one or more selected from a group consisting of ginkgo leaf extract and red ginseng extract.

12. The composition according to claim 8, wherein the composition comprises:
0.01-3 wt % of prolamin;
0.01-5 wt % of pullulan; and
0.01-2 wt % of pectin,
based on the total weight of the composition.

13. The composition according to claim 8, wherein the insoluble effective substance is comprised in an amount of 0.01-10 wt % based on the total weight of the composition.

14. A method for one or more of skin barrier enhancement, skin moisturization and skin regeneration, which comprises administering an effective amount of the composition according to claim 8 to a subject in need thereof.

15. The method according to claim 8, wherein the composition is a cosmetic composition.

16. A method for preparing the structure according to claim 1, comprising:
   a step of forming a core by dispersing prolamin in an alcohol solvent;
   a step of forming a shell surrounding the core by adding pullulan onto the alcohol solution in a drop-by-drop manner;
   a step of coating pectin on an outermost layer of the shell and forming a network between the shell by adding pectin to the pullulan-added alcohol solution; and
   a step of obtaining a solution with a core-shell network structure dissolved in an aqueous phase formed by evaporating the alcohol from the pectin-added solution.

17. A method for stabilizing an insoluble effective substance by the structure according to claim 1, comprising:
   a step of forming a core by dispersing prolamin and an insoluble effective substance in an alcohol solvent;
   a step of forming a shell surrounding the core by adding pullulan onto the alcohol solution in a drop-by-drop manner;
   a step of coating pectin on an outermost layer of the shell and forming a network between the shells by adding pectin to the pullulan-added alcohol solution; and
   a step of obtaining a solution with a core-shell network structure dissolved in an aqueous phase by evaporating the alcohol from the pectin-added solution.

18. The method according to claim 17, wherein the step of forming the network between the shells further comprises a step of gelating the solution with the core-shell network structure formed by adjusting the acidity of the alcohol solution to pH 2.5-6.5.

19. The method according to claim 17, wherein the temperature in the step of evaporating the alcohol is 20-40° C.

20. The method according to claim 17, wherein the insoluble effective substance is a hydrophobic and alcohol-soluble substance.

* * * * *